United States Patent [19] [11] Patent Number: 4,850,231
Ralfs et al. [45] Date of Patent: Jul. 25, 1989

[54] COMPRESSION TEST MACHINES

[75] Inventors: Colin A. Ralfs; Anthony Murdock, both of Preston, England

[73] Assignee: British Aerospace Public Limited Company, London, England

[21] Appl. No.: 219,396

[22] Filed: Jul. 15, 1988

[30] Foreign Application Priority Data

Jul. 18, 1987 [GB] United Kingdom ............... 8716989

[51] Int. Cl.$^4$ ............................................. G01N 3/04
[52] U.S. Cl. ......................................... 73/859; 73/818
[58] Field of Search ....................... 73/859, 818, 856; 269/217, 256

[56] References Cited

U.S. PATENT DOCUMENTS 2,447,660 8/1948 Miklowitz ...................... 269/217 X
3,757,568 9/1973 Fletcher et al. .

FOREIGN PATENT DOCUMENTS 3537248 4/1987 Fed. Rep. of Germany .
238440 10/1987 Japan ..................................... 73/818
WO83/03003 1/1983 PCT Int'l Appl. .
1132815 11/1968 United Kingdom .

Primary Examiner—Jerry W. Myracle
Attorney, Agent, or Firm—Cushman, Darby & Cushman

[57] ABSTRACT

A stabilization and gripping device for use with a compression test machine to measure strain vs load characteristics of, in particular composite material uni-directional ply specimens, includes a guide sleeve, two hollow open ended end-blocks adapted to slidably fit within the guide sleeve and to co-operate with parts of the machine for applying compressive forces to the specimen, and two pairs of collets each pair for gripping a separate one of two ends of the specimen, the collets having a planar gripping inner surface, at least one outer surface tapered with respect to the gripping surface and corresponding to a tapered inner surface of the end blocks, and a planar outer surface for co-operation with a substantially planar inner surface of the end blocks so that the collets may be non-rotatably inserted in the end blocks in a position in which the respective inner surfaces are parallel and pairs of the inner surfaces define a location for the specimen ends.

7 Claims, 3 Drawing Sheets

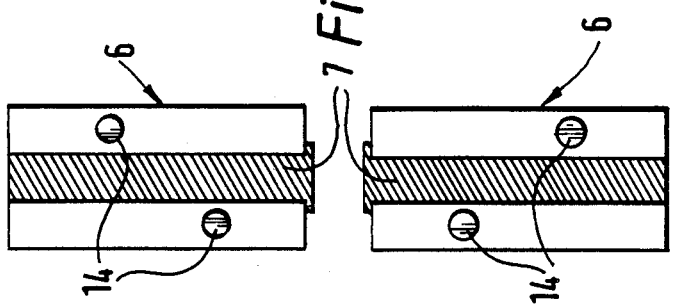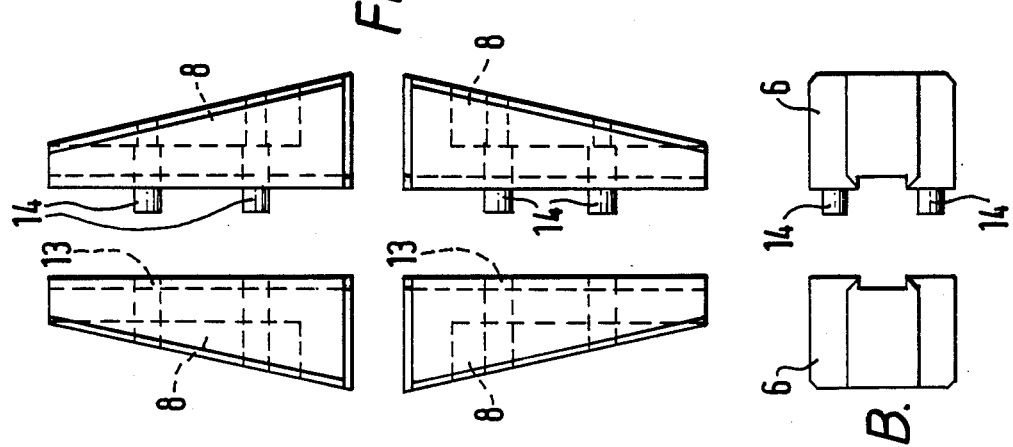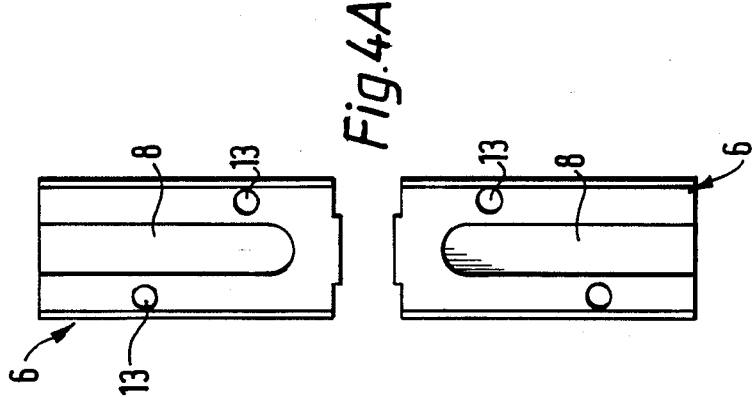

COMPRESSION TEST MACHINES

COMPRESSION TEST MACHINES

This invention relates to compression test machines and in particular to accessories for such machines to be used for gripping and stabilizing a specimen during a compression test. The invention has particular application to machines intended for compression of specimens of composite materials comprising uni-directional plies.

It is established practice to test materials for their compressive strength by placing a specimen of the material in the jaws of a hydraulic press, compressing the sample, and, at the same time, monitoring the resultant deformation of the specimen with suitable electrical transducers to derive its strain vs load characteristics. However, difficulties arise when attempting to measure the characteristics of materials of high compressive strength such as carbon fibre or composites of the type manufactured by Du-pont and sold under their registered trade mark KEVLAR.

Loads typically of the order of 20-30 Kn have to be applied to uni-directional carbon fibre composites before they compress appreciably. The physical extent of their compression is even then very small and difficult to measure accurately even with the most sensitive electrical strain gauges. In known test machines each specimen, which is generally in the form of a strip of rectangular cross section of the material concerned and having standardized dimensions, is clamped at both ends in such a way that a relatively small portion only of the specimen is left unsupported between the two clamps. It is the behaviour of this unsupported region of specimen which is measured during compression. The unsupported length of specimen is kept as short as possible to minimize buckling of the specimen during compression. The unsupported region must however be long enough to allow transducers to be connected to the specimen. The shortest unsupported length of specimen to which an extensometer bridge can practically be attached is about 10 mm. The axial length reduction of a specimen of composite material during compression is considerably less than 10 mm.

It is known to clamp composite material specimens at each end by means of collet and end block arrangements in which the collets grip the specimen increasingly tightly in response to increasing compressive forces applied to the end-blocks.

The collets have tapered and rounded outer surfaces corresponding to suitably machined inner surfaces of the end-blocks. In known examples the Cellanese Corporation have produced frusto conical collets and NASA describe a cylindrical arrangement in their U.S. Pat. No. 3,757,568. However a drawback with these arrangements is that the collets may take up a different rotational orientation with respect to the end-blocks at each fitting to the specimen leading to so called "clamping errors". Each rotational orientation can cause a slightly different deformation, such as twisting, of the specimen during compression and these differences may cause the plies to be loaded in different ways giving rise to inconsistent results. Because of the random nature of clamping errors they are very difficult to eliminate or average out.

It is an object of the present invention to provide improved stabilization and gripping devices for clamping a specimen of material in a compression test machine which will reduce slippage between the specimen and the clamps and which may be repeatedly dismantled and re-assembled without affecting the consistency with which the specimen is gripped and without affecting the reliability and comparability of the results of successive tests with the same or different specimens.

According to one aspect of this invention there is provided a specimen stabilization and gripping device for use with a compression test machine for the compression testing of specimens comprising strips of material of rectangular cross section including a guide sleeve, two hollow open ended end-blocks adapted to slidably fit within the guide sleeve and to co-operate with parts of the machine for applying compressive forces to the specimen, and two pairs of collets each pair for gripping a separate one of two ends of the specimen, said collets having a planar gripping inner surface, at least one outer surface tapered with respect to said gripping surface and corresponding to a tapered inner surface of said end-blocks, and a planar outer surface for co-operation with a substantially planar inner surface of said end blocks so that said collets may be non-rotatably inserted in said end-blocks in a position in which the respective inner surfaces of each pair are parallel and define a location for the specimen ends.

The collets may be of any cross section which defines at least one planar surface in addition to said planar gripping surface. For example the collets may have a rectangular cross section or a triangular cross section. Naturally the end-blocks must then have a corresponding inner cross section and the cross section of both end-block inner and collet outer surfaces must taper axially with respect to the longitudinal axis of the specimen.

The outer sleeve is preferably, but not essentially cylindrical and the end-blocks must have a corresponding outer surface shape so as to be slidably mountable therein.

Preferably the end-blocks are provided with adjusting means for adjusting the plane of the gripping surfaces of the inserted collets. The adjusting means may comprise grub screws arranged to pass through and protrude from the inner surface of each end-block in a direction transverse to the plane of the gripping surfaces of the collets. When the collets are inserted in the end blocks the grub screws will then bear on their outer surfaces and may be tightened or loosened to effect the adjustment. Preferably the outer surface of each collet is then provided with a 'flat' on the appropriate outer surface, parallel to the gripping surface, so that the grub screws bear on a surface normal to their direction of travel rather than on a tapered surface.

A specific embodiment of the present invention will now be described by way of example only and with reference to the following drawings of which:

FIGS. 4A-4D are top, end, side and bottom views of the collets of FIG. 4, and;

Figure 1:
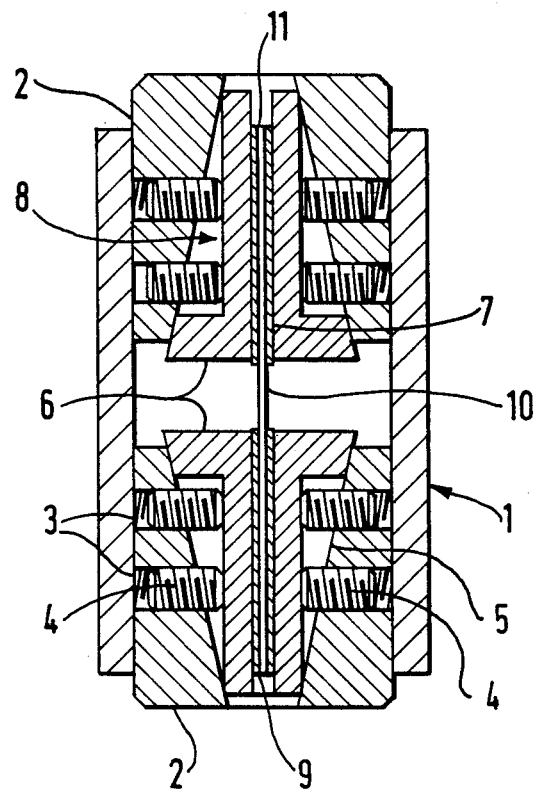
FIG. 1 is a section view of a specimen stabilization and gripping device.
Figure 3:
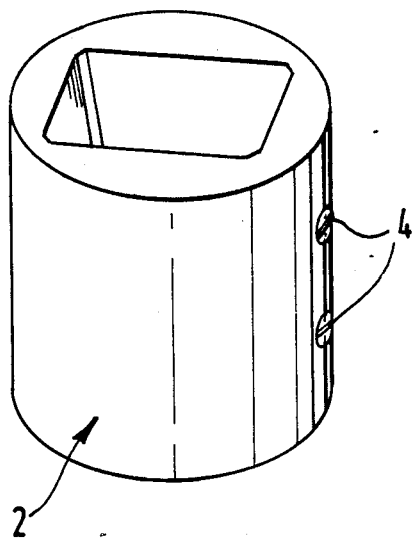
FIG. 3 is a perspective view of an end-block forming part of the device of FIG. 1.
Figure 5:
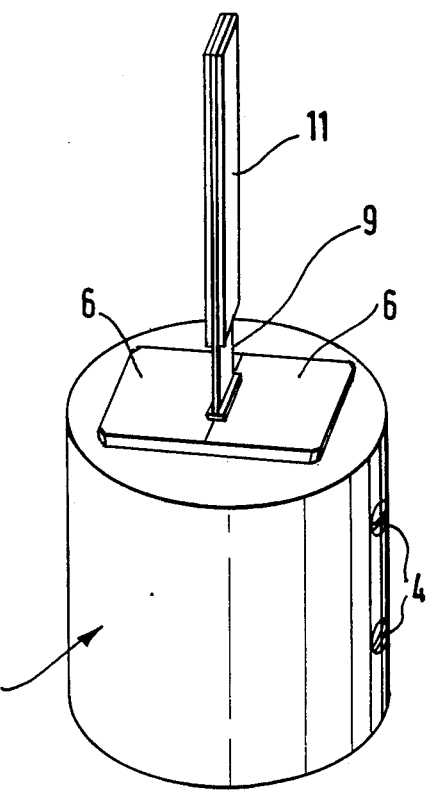
FIG. 5 is a perspective view of part of the device of FIG. 1 assembled round a specimen to be tested.
Figure 4:
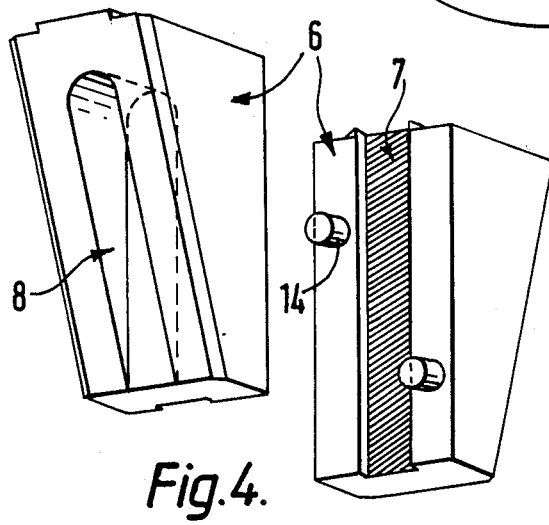
FIG. 4 is a perspective view of a collet pair, for use with the device of FIG. 1.

Referring to FIG. 1 a stabilization and gripping device for use with a compression test machine comprises a guide cylinder 1 in which two cylindrical end-blocks 2 are slideably mounted. The guide cylinder is hollow and has an internal diameter which is slightly larger than the external diameter of the end blocks. The end-blocks 2, as will be seen more clearly in FIG. 3, have opposing threaded bore pairs 3 extending from their outer cylindrical surfaces to their interiors and into which grub screws 4 are screwed. The interior of each end-block 2 is a tapered cavity of truncated wedge shape 5 in which a pair of collets 6 is seated. The cavity 5 of each end-block is of the same size and same rectilinear cross-sectional shape as each of the pair of collets. The collets each have a roughened surface 7 for gripping the specimen and a slot or groove 8 in their outer surface against which the grub screws 4 abut. A specimen 9 comprising a uni-directional composite strip of rectangular cross section is gripped at both ends between the collets so that a short portion 10 is left unsupported. The specimen has pads or tabs 11 of friction material bonded to its ends to improve gripping of the specimen. The pads 11 preferably have spark eroded surfaces patterned to give improved friction properties in relation to an opposite pattern forming the roughened surface of the collets which grip them.

Figure 2:
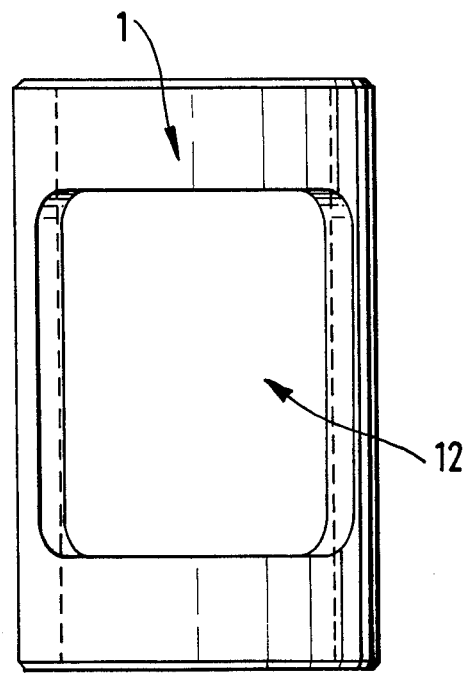
FIG. 2 is a partial perspective view through a guide sleeve forming part of the device of FIG. 1.

FIG. 2 shows the guide sleeve 1 to have a large aperture 12 extending therethrough. This aperture allows viewing of the specimen while it is under test and enables transducers to be attached to the unsupported region 10 of the specimen. The aperture also reduces the thermal mass of the guide sleeve 1 and improves the accuracy of tests conducted when the specimen is heated to different temperatures.

FIGS. 4 and 4A–4D show the collets 6 in more detail. The collets are arranged as matched pairs to ensure that differences in tolerances between the parts always remain constant in successive tests. The collets in each pair are labelled to make it easier to identify and match the parts of each pair but as a further precautionary measure each collet pair has a diagnonal peg and hole arrangement. One collet in each pair has a pair of pegs or dowels 14 which are positioned diagonally across and on either side of the surfaces 7. The other collet of the same pair has a pair of corresponding holes 13 with which the pegs 14 co-operate in use. The pegs and hole of one collet pair are arranged as diagonal opposites of the pegs and holes of the other collet pair so that the pairs are not interchangeable and cannot be inadvertantly mismatched.

Operation of the invention is now described with reference to all the drawings in which common features have been given identical reference numerals.

A specimen 9 of composite material is placed in between matching pairs of collets 6 so the roughened surfaces 7 press against and grip the tabs 11 of friction material. The collets 6 are the clipped together around the specimen by engaging the pegs 14 with the appropriate holes 13. The collets are then placed inside the cavities 5 of the end-blocks 2. As each of the collet pairs are slid exially inwardly into the cavity 5 of each end-block 2 their shape causes them to move together, by wedge action, to grip the specimen between them. The rectangular cross section of the collets and end-block cavities ensure that the collets can only be placed into each end block in one fixed orientation and this minimizes clamping errors between successive tests.

Next grub screws 4 are tightened into the bores 3 until they abut against the grooves 8 of the collets. The grub screws are tightened until they retain the collets in the end piece and they are also used as a fine adjustment to change the angle at which each collet pair seats on the specimen within the cavity of each end-block. When the specimen 9 is clamped securely in place between the end-blocks 2 the assembly is placed inside guide cylinder 1 by sliding it through one of the open ends of the cylinder. If the two end-blocks do not slide freely inside the guide cylinder it is an indication that the collet/end-block assemblies at each end of the specimen are gripping the specimen in slight misalignment with respect to each other and this could give spurious results.

In this event the grub screws 4 at the sides of the end-blocks 2 are adjusted until the end-blocks slide freely within the guide cylinder.

The guide cylinder is then placed between the jaws (not shown) of the compression machine and compression machine plattens (not shown) are gently moved into contact with the face of each of the end-blocks 2. An extensometer bridge (not shown) is then placed through the aperture 12 of the guide sleeve and clamped to the unsupported region 10 of the specimen.

A load is then applied to the ends of the specimen and the amount of deformation of the unsupported region of the specimen is measured as strain vs load. When the compression test has been completed the specimen is removed by a reversal of the sequence just described.

Although only one specific embodiment of the invention has been disclosed other arrangements are possible without departing from the scope of the invention. For example the collets need not be of rectangular cross section as shown in the figures but could have any number of sides or be any shape as long as they have at least one planar surface co-operating with a similar planar surface in the end-block for the purposes of consistent alignment at each assembly operation. For example the collets could be of triangular cross section.

We claim:

1. A specimen stabilization and gripping device for use with a compression test machine for the compression testing of specimens comprising strips of material of rectangular cross section including a guide sleeve, two hollow open ended end-blocks adapted to slidably fit within the guide sleeve and to co-operate with parts of the machine for applying compressive forces to the specimen, and two pairs of collets each pair for gripping a separate one of two ends of the specimen, said collets having a planar gripping inner surface, at least one outer surface tapered with respect to said gripping surface and corresponding to a tapered inner surface of said end blocks, and a planar outer surface for co-operation with a substantially planar inner surface of said end blocks so that said collets may be non-rotatably inserted in said end blocks in a position in which the respective inner surfaces are parallel and pairs of said inner surfaces define a location for the specimen ends.

2. A specimen stabilization and gripping device as claimed in claim 1 and wherein the collets have a rectangular cross-section.

3. A specimen stabilization and gripping device as claimed in claim 2 and wherein the guide sleeve is of cylindrical form.

4. A specimen stabilization and gripping device as claimed in claim 1 and wherein the collets have a triangular cross-section.

5. A specimen stabilization and gripping device as claimed in claim 1 and wherein the guide sleeve is of cylindrical form.

6. A specimen stabilization and gripping device as claimed in claim 4 and wherein the guide sleeve is of cylindrical form.

7. A specimen stabilization and gripping device as claimed in claim 1, 2, 4, 5, 3, or 6 and wherein the endblocks are provided with adjusting means for adjusting the plane of the gripping surfaces of the collets when inserted therein.

* * * * *